US012799473B2

(12) United States Patent

Han et al.

(10) Patent No.: US 12,799,473 B2
(45) Date of Patent: Nov. 17, 2026

(54) PORTABLE DEVICE FOR ISOLATING NUCLEIC ACID FROM BLOOD

(71) Applicants: KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

(72) Inventors: Hyungsoo Han, Daegu (KR); Youngmi Lee, Daegu (KR); Mijung Bae, Daegu (KR)

(73) Assignees: KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

( * ) Notice: Subject to any disclaimer, the term of this patent is extended or adjusted under 35 U.S.C. 154(b) by 481 days.

(21) Appl. No.: 18/222,397

(22) Filed: Jul. 14, 2023

(65) Prior Publication Data

US 2023/0357749 A1 Nov. 9, 2023

Related U.S. Application Data

(63) Continuation-in-part of application No. PCT/KR2022/017732, filed on Nov. 11, 2022.

(30) Foreign Application Priority Data

May 3, 2022 (KR) ........................ 10-2022-0054714

(51) Int. Cl.

| | |
|---|---|
| ***C12N 15/10*** | (2006.01) |
| ***B01D 57/02*** | (2006.01) |
| ***G01N 27/447*** | (2006.01) |

(52) U.S. Cl.

CPC ........... *C12N 15/101* (2013.01); *B01D 57/02* (2013.01); *C12N 15/1003* (2013.01); *G01N 27/44713* (2013.01)

(58) Field of Classification Search

CPC .................................................... C12N 15/101

See application file for complete search history.

(56) References Cited

U.S. PATENT DOCUMENTS

2010/0029915 A1 2/2010 Duthie et al.

FOREIGN PATENT DOCUMENTS

| | | | |
|---|---|---|---|
| EP | 2700712 | A1 | 2/2014 |
| KR | 10-2000-0018854 | A | 4/2000 |

(Continued)

OTHER PUBLICATIONS

Kohlheyer et al., "Bubble-Free Operation of a Microfluidic Free-Flow Electrophoresis Chip with Integrated Pt Electrodes" Anal Chem vol. 80 pp. 4111-4118, DOI:10.1021/ac800275c (Year: 2008).*

(Continued)

*Primary Examiner* — Andrea Olson

(74) *Attorney, Agent, or Firm* — Bridgeway IP Law Group, PLLC; Sang Ho Lee; Hyun Woo Shin

(57) ABSTRACT

Provided is a portable device for isolating nucleic acid from blood. The portable device for isolating nucleic acid from blood includes a body, a channel that is formed on an upper surface of the body in a groove shape with a set standard and provides a path for moving the blood, a pair of platinum wires of which ends are in contact with both ends of the channel, and a battery of which both electrodes are connected to the other ends of the pair of platinum wires and (Continued)

which provides an electrical force, wherein the blood dropped into the channel in contact with the platinum wire connected to a negative electrode of the battery is moved toward the channel in contact with the platinum wire connected to a positive electrode of the battery due to the electrical force provided by the battery so that the nucleic acid is isolated from the blood.

8 Claims, 4 Drawing Sheets

(56) References Cited

FOREIGN PATENT DOCUMENTS

| | | | |
|---|---|---|---|
| KR | 10-0845971 | B1 | 7/2008 |
| KR | 10-1001747 | B1 | 12/2010 |
| KR | 10-2014-0026400 | A | 3/2014 |
| KR | 2014-236742 | A | 12/2014 |
| KR | 10-2018-0073353 | A | 7/2018 |
| KR | 10-1915675 | B1 | 11/2018 |
| KR | 10-2022-0031539 | A | 3/2022 |
| KR | 10-2022-0075978 | A | 6/2022 |
| KR | 10-2500163 | B1 | 2/2023 |

OTHER PUBLICATIONS

Bocek et al., "Instrumentation for High-Speed Isotachophoresis" Journal of Chromatography vol. 106 pp. 283-290 (Year: 1975).*
Sonnenberg et al., "Dielectrophoretic isolation of DNA and nanoparticles from blood" Electrophoresis vol. 33 pp. 2482-2490, DOI: 10.1002/elps.201100700 (Year: 2012).*
Sullivan et al., "Nucleic acid sample preparation from whole blood in a paper microfluidic device using isotachophoresis" Journal of Chromatography vol. 1163 No. 122494, DOI:10.1016/j.chromb.2020.122494 (Year: 2021).*
Hügle, Matthias et al., "A lab-on-a-chip for the extraction of bacterial nucleic acids from whole human blood", 20th International Conference on Solid-state Sensors, Actuators and Microsystems & Eurosensors XXXIII (Tranducers & Eurosensors XXXIII), IEEE, Jun. 23, 2019, pp. 925-927.
Chan, Ho Nam et al., "Point-of-care testing: applications of 3D printing", Lab on a Chip, 2017, vol. 17, No. 16, pp. 2713-2739.
Yang, Jun et al., "A microfluidic device for rapid quantification of cell-free DNA in patients with severe sepsis", Lab on a Chip, 2015, vol. 15, No. 19, pp. 3925-3933.

* cited by examiner

PORTABLE DEVICE FOR ISOLATING NUCLEIC ACID FROM BLOOD

CROSS-REFERENCE TO RELATED APPLICATION

This application is a continuation-in-part application of PCT international application No. PCT/KR2022/017732, filed on Nov. 11, 2022, and claims priority to Korean patent application No. 10-2022-0054714, filed on May 3, 2022, the entire disclosures of which are incorporated herein by reference.

TECHNICAL FIELD

The present invention relates to a portable device for isolating nucleic acid from blood, and more particularly, a portable device for isolating nucleic acid from the blood, which is capable of extracting and isolating nucleic acid from blood without separate preprocessing.

BACKGROUND ART

Blood contains various components, including cells such as white blood cells and red blood cells, cell-derived small particles such as platelets and exosomes, plasma proteins and lipids, nucleic acid fragments or metabolites, and the like.

When individual components of the blood are measured, health conditions and diseases may be diagnosed, and thus the blood is used as a useful biological sample for diagnosis. Among them, a genomic deoxyribonucleic acid (DNA) of a blood sample may be used to diagnose human health conditions and the presence or absence of diseases. Therefore, extraction of nucleic acid from the blood in a laboratory is important for performing molecular research application programs.

For the extraction of the nucleic acid from the blood, it is essential to select a method suitable for the situation. In general, various devices and reagents are widely used to isolate nucleic acid components from the blood, but it is difficult to perform a polymerase chain reaction (PCR) directly using whole blood, and thus a laboratory-level processing procedure of isolating the blood components should be performed in advance. That is, the technique of separating blood into pure components and measuring them individually has limitations that require time and complex procedures requiring equipment and reagents.

However, for on-site diagnosis, it is essential to select an appropriate extraction method satisfying rapidity, cost-effectiveness, and technical requirements. Even in previous research, PCR analysis directly using the blood without experimental procedures such as DNA extraction and purification has been attempted. However, these experiment methods are still difficult due to PCR inhibitors induced by blood compounds.

Thus, it is necessary to develop a device that is portable for the on-site diagnosis and easily and conveniently isolates the nucleic acid from the whole blood.

Korean Patent Application Publication No. 10-2014-0026400 (published on Mar. 5, 2014) discloses the background technology of the present invention.

DISCLOSURE

Technical Problem

The present invention is directed to providing a portable device for isolating nucleic acid from blood capable of extracting and isolating nucleic acid from blood without separate preprocessing.

Technical Solution

One aspect of the present invention provides a portable device for isolating nucleic acid from blood, the portable device including a body, a channel that is formed on an upper surface of the body in a groove shape with a set standard and provides a path for moving the blood, a pair of platinum wires of which ends are in contact with both ends of the channel, and a battery of which both electrodes are connected to the other ends of the pair of platinum wires and which provides an electrical force, wherein the blood dropped into the channel in contact with the platinum wire connected to a negative electrode of the battery is moved toward the channel in contact with the platinum wire connected to a positive electrode of the battery due to the electrical force provided by the battery so that the nucleic acid is isolated from the blood.

The channel may allow the battery to apply a voltage to the groove through the pair of platinum wires in contact with a buffer solution filling the groove so as to move non-preprocessed nucleic acid in the blood, and the nucleic acid may move from the negative electrode to the positive electrode due to electrical properties and thus may be separated from the blood when the voltage is applied to the nucleic acid.

The channel may be formed of a material and shape that allow the buffer solution to be introduced into the groove, and the buffer solution may be a physiological saline solution.

A substance moved toward the channel in contact with the platinum wire connected to the positive electrode within a set time when a certain voltage is applied to the channel through the battery may be determined to be the nucleic acid.

The ends of the pair of platinum wires may be in contact with the channel, which are immersed in the buffer solution and have a preset length and a preset thickness.

The channel may be implemented in any of various shapes and implemented such that a width, a length, and a depth of the channel are set to be smaller than those of the body.

The body may be an electrophoresis device implemented using a three-dimensional (3D) printer and made of a non-flammable material through which a current does not flow.

Advantageous Effects

As described above, according to the present invention, a portable device can quickly isolate nucleic acid components from blood without separate preprocessing, which is useful in diagnosis, can be simple to use and portable, and secure on-site performance and effectiveness.

Further, according to the present invention, a process of isolating the nucleic acid from the whole blood using the electrophoresis device is not difficult, used buffers can be easily purchased in the market by ordinary people, and thus user satisfaction can be improved.

Further, according to the present invention, since the portable device can be easy to use without separate reagent preprocessing for the blood, PCR inhibitors generated when the whole blood is directly used can be removed and an influence on a diagnostic result using the nucleic acid can be minimized.

Further, according to the embodiment, the portable device is small and light and thus easily moves, has a simple structure that does not affect the diagnostic result due to damage to the portable device, and has a low price, high user convenience, and a short process time and thus has a high potential for commercialization.

MODES OF THE INVENTION

Figure 1:
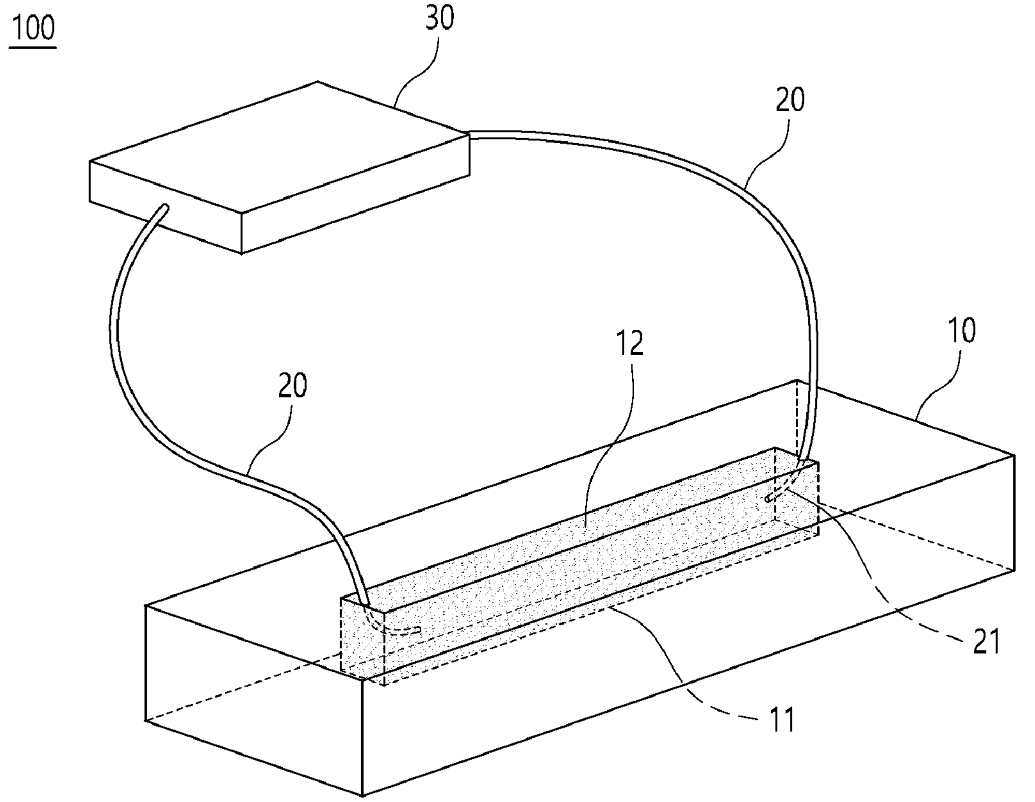
FIG. 1 is a perspective view illustrating a portable device for isolating nucleic acid from blood according to an embodiment of the present invention.

Hereinafter, embodiments of the present invention will be described in detail with reference to the accompanying drawings. In this process, the thickness of lines or the size of components illustrated in the drawings may be exaggerated for clarity and convenience of description.

Further, the terms described below are defined in consideration of functions in the present disclosure and may change according to the intention or custom of a user or an operator. Therefore, definitions of these terms should be made based on the contents throughout the present specification.

Hereinafter, embodiments of the present disclosure will be described in more detail with reference to the drawings.

A portable device for isolating nucleic acid from blood according to an embodiment of the present invention will be described with reference to FIGS. 1 to 5.

Figure 2:
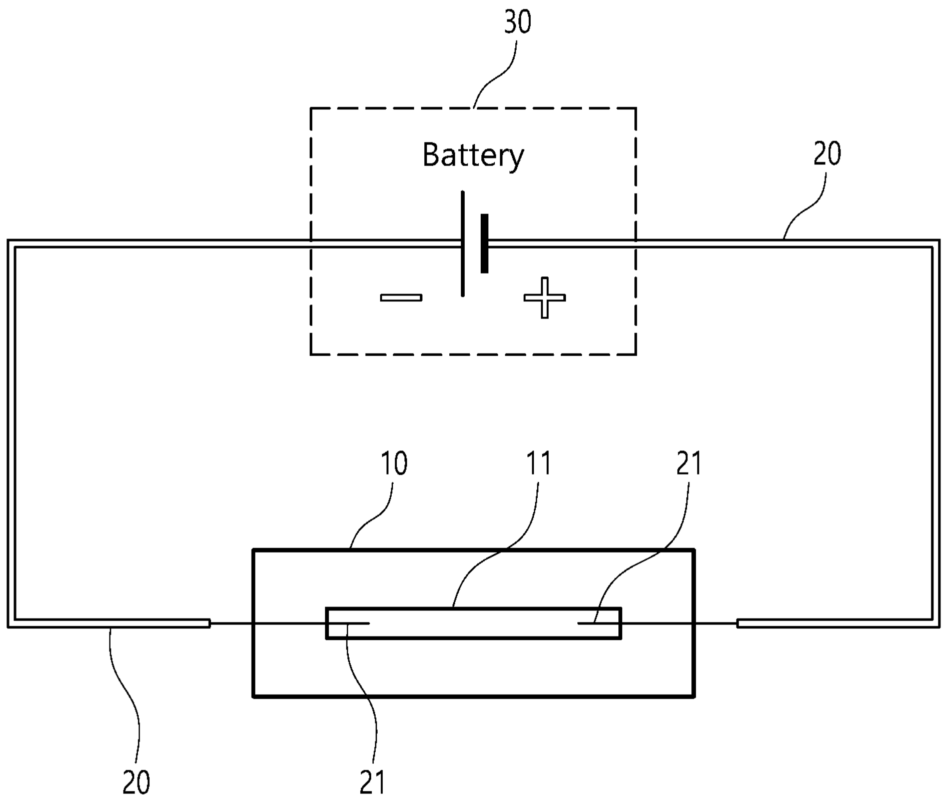
FIG. 2 is a schematic view of FIG. 1.

FIG. 1 is a perspective view illustrating a portable device for isolating nucleic acid from blood according to an embodiment of the present invention, and FIG. 2 is a schematic view of FIG. 1.

As illustrated in FIGS. 1 and 2, a portable device 100 for isolating nucleic acid from blood according to the embodiment of the present invention, includes a body 10, a channel 11, a platinum wire 20, and a battery 30.

First, the body 10 is adapted to isolate the nucleic acid from the blood and may be implemented as a diagnostic kit having a portable size.

In this case, the body 10 may be an electrophoresis device implemented using a three-dimensional (3D) printer and made of a non-flammable material through which a current does not flow.

Further, the channel 11 is formed on an upper surface of the body 10 in a groove shape with a set standard and provides a path for moving the blood.

In this case, the channel 11 allows the battery 30 to apply a voltage to the groove through a pair of platinum wires 20 in contact with a buffer solution 12 filling the groove so as to move the non-preprocessed nucleic acid in the blood.

Thus, the channel 11 may be formed of a material and shape capable of introducing the buffer solution 12 into the groove.

In this case, the buffer solution 12 may be a physiological saline solution.

Further, the channel 11 may be implemented in any of various shapes and may be implemented such that the width, the length, and the depth thereof are set to be smaller than those of the body 10.

Figure 3:
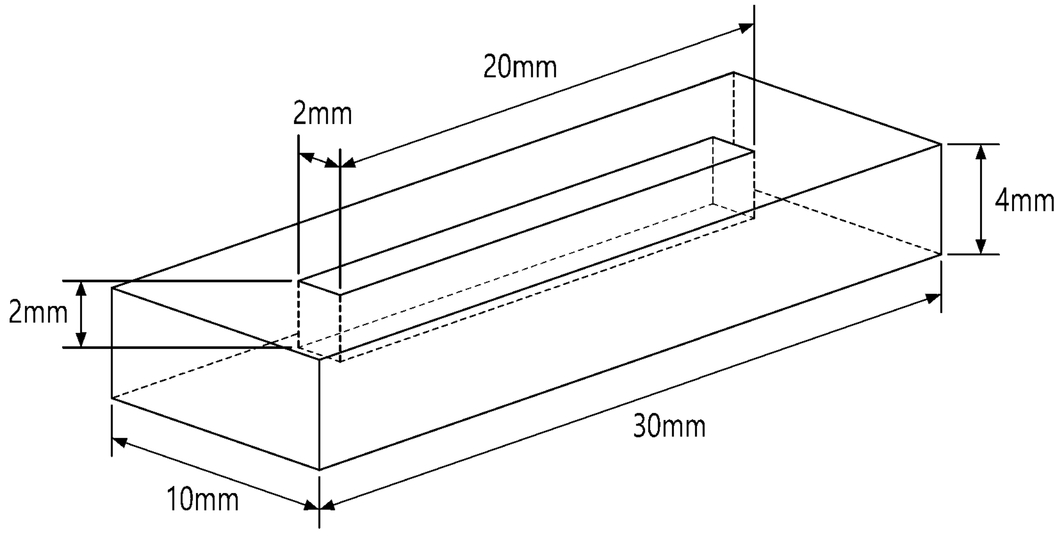
FIG. 3 is a view illustrating specifications of a body and a channel illustrated in FIG. 1.

FIG. 3 is a view illustrating specifications of a body and a channel illustrated in FIG. 1.

As illustrated in FIG. 3, when the body 10 has a width of 30 mm, a length of 10 mm, and a height (depth) of 4 mm, the channel 11 may have a width of 20 mm, a length of 2 mm, and a height (depth) of 2 mm, but the present invention is not limited thereto.

Further, the platinum wires 20 are provided as a pair, so that ends 21 thereof are in contact with both ends of the channel 11, and the other ends thereof are connected to both electrodes of the battery 30.

In this case, a portion connected to the battery 30 may be a general cable such as a clamp cable, and only a material of each of the ends 21 in contact with both ends of the channel 11 may be platinum.

That is, as illustrated in FIGS. 1 and 2, only the ends 21 of the platinum wires 20, which are immersed in the buffer solution 12 filling the channel 11 may be made of platinum, and the other portions thereof may be made of any material as long as the material may allow the battery to apply the voltage to the channel 11.

Further, the ends 21 of the pair of platinum wires 20 may have a preset length and a preset thickness.

In this case, the ends 21 of the platinum wires 20 immersed in the buffer solution 12 may be manufactured with a standard in which the length is 5 mm and the thickness (diameter) is 0.3 mm, but the present invention is not limited thereto, Finally, the battery 30 is connected to the other ends of the pair of platinum wires 20 to provide an electrical force.

Figure 4:
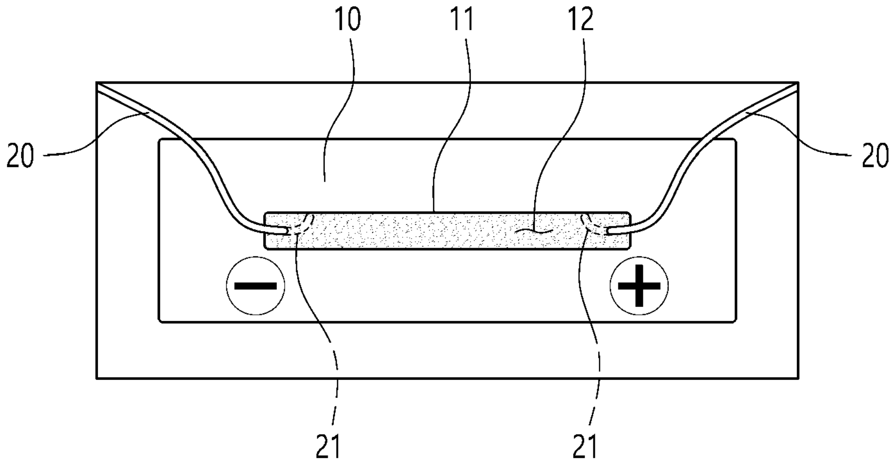
FIG. 4 is a schematic view illustrating a real example of the body illustrated in FIG. 1.

FIG. 4 is a schematic view illustrating a real example of the body illustrated in FIG. 1.

As illustrated in FIG. 4, the body 10 may be manufactured using the 3D printer (SMART3D Printer) and may be manufactured in a portable size. In this case, the channel 11 is filled with the buffer solution 12, the ends 21 of the pair of platinum wires 20 are in contact with both ends of the channel 11, and thus the voltage is applied to the buffer solution 12.

Figure 5:
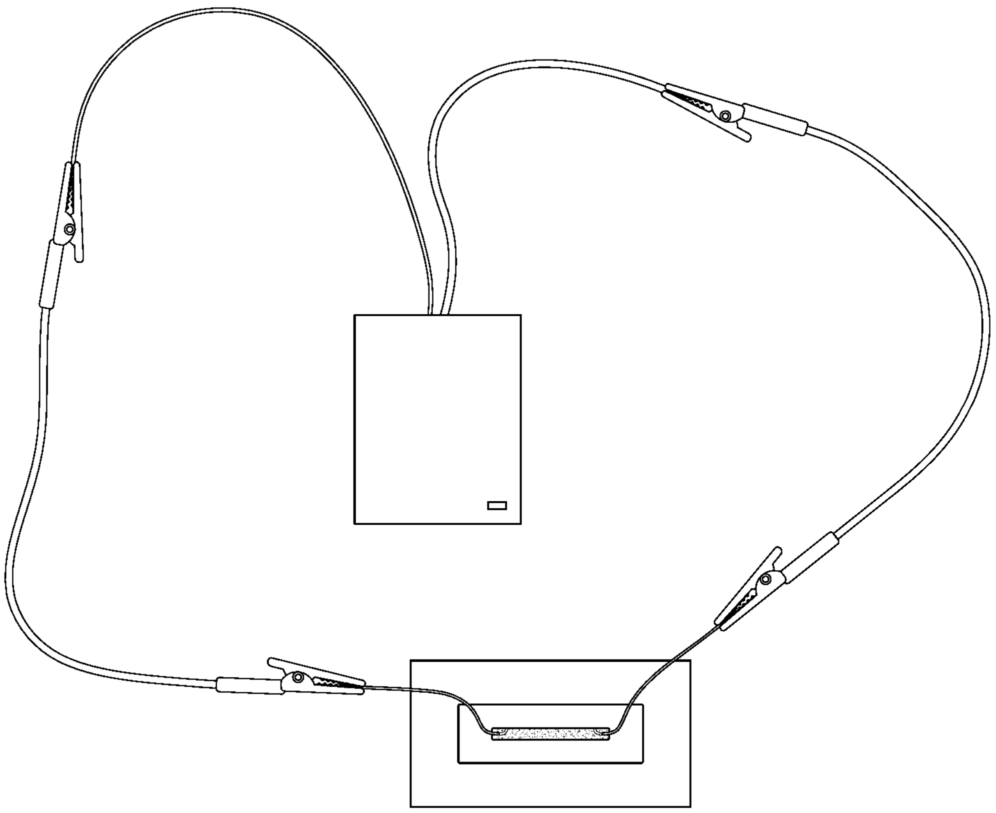
FIG. 5 is a view illustrating a real example of the portable device for isolating nucleic acid from blood according to the embodiment of the present invention.

FIG. 5 is a view illustrating a real example of the portable device for isolating nucleic acid from blood according to the embodiment of the present invention.

As illustrated in FIG. 5, the portable device 100 for isolating nucleic acid from blood according to the embodiment of the present invention is a portable device for isolating only the nucleic acid from a small amount of a non-preprocessed blood sample. The blood dropped into the channel 11 in contact with the platinum wire 20 connected to a negative electrode of the battery is moved toward the channel 11 in contact with the platinum wire 20 connected to a positive electrode of the battery 30 due to the electrical force provided by the battery 30 so that the nucleic acid is isolated from the blood.

In detail, a substance moved toward the channel 11 in contact with the platinum wire 20 connected to the positive electrode within a set time when a certain voltage is applied to the channel 11 through the battery 30 is determined to be the nucleic acid.

In detail, when the collected blood is put into the buffer solution 12 filling the channel 11, components of the blood are broken, and when a current flows in the buffer solution 12, charged materials move from the negative electrode to the positive electrode. In this case, since the nucleic acid, which is the lightest among various substances in the blood, first moves toward the positive electrode, the substance that arrives first, that is, arrives at the fastest time, can be determined to be the nucleic acid.

In this case, since the nucleic acid has an electric charge, when the blood is dropped and the voltage is applied thereto, the nucleic acid moves from the negative electrode to the positive electrode due to electrical properties and thus is separated from the blood.

Meanwhile, the amount of the blood sample that may be applied to the portable device 100 according to the present embodiment may be about 1.0-3.0 ul, preferably, about 2 ul, and all blood samples that is preprocessed through a lysis buffer method and/or incubation may be adopted as the blood sample.

In more detail, the blood sample that may be applied to the portable device 100 according to the present embodiment may be a sample preprocessed by the lysis buffer method of mixing the whole blood and a lysis buffer and/or by incubating the whole blood at a predetermined temperature and during a predetermined time. For example, the blood sample may be a sample incubated at about 55-60° C. for about 8-20 minutes, preferably, about 56° C. for about 10 minutes.

The blood sample should be precisely dropped at a designated position in the channel 11 through a micro pallet. The designated position in the channel 11 may be a position in which the blood may be well mixed into the buffer solution 12 in the channel 11 and a position within a predetermined distance from an electrode. According to the present embodiment, the position may be a position in the channel 11 within a predetermined distance from the one end 21 of the platinum wire 20 with which the platinum wire 20 connected to the negative electrode is in contact and preferably may be a position in the channel 11 within about 0.5-1.5 mm, preferably 1 mm from the one end 21 of the platinum wire 20.

Meanwhile, a substance determined as the nucleic acid moved to the channel 11 with which the platinum wire 20 connected to the positive electrode is in contact within a set time may be collected in the form of a solution. The amount of the solution may be small, preferably, about 1 ul.

That is, after electricity flows, a small amount of solution containing the nucleic acid is collected from the designated position in the channel 11 on the positive electrode side and is used for genetic testing. In this case, the designated position may be a position in which the solution containing the nucleic acid may be collected and a position spaced a predetermined distance from the electrode. According to the present embodiment, the position may be a position in the channel 11 spaced a predetermined distance from the one end 21 of the platinum wire 20 with which the platinum wire 20 connected to the positive electrode is in contact and preferably, may be a position in the channel 11 spaced about 5 mm to 10 mm from the one end 21 of the platinum wire 20.

As described above, the portable device for isolating nucleic acid from blood according to the embodiment of the present invention can be usefully used for diagnosis by quickly isolating the nucleic acid from blood without separate preprocessing, and can secure on-site performance and effectiveness because the portable device is simple to use and is portable.

Further, according to the embodiment of the present invention, a process of isolating the nucleic acid from the whole blood using the electrophoresis device is not difficult, the used buffers may be easily purchased in the market by ordinary people, and thus user satisfaction can be improved.

Further, according to the embodiment of the present invention, since the portable device may be simply used without separate reagent preprocessing for the blood, PCR inhibitors generated when the whole blood is directly used can be removed and an influence on a diagnostic result using the nucleic acid can be minimized.

Further, according to the embodiment, the portable device is small and light and thus easily moves, has a simple structure that does not affect the diagnostic result due to damage to the portable device, and has a low price, high user convenience, and a short process time and thus has a high potential for commercialization.

Although the present invention has been described with reference to embodiments illustrated in the drawings, the description is merely illustrative, and those skilled in the art to which the technology belongs should understand that various modifications and other equivalent embodiments may be made. Thus, the true technical scope of the present invention should be determined by the technical spirit of the appended claims.

| [Description of reference numerals] | |
|---|---|
| 100: Portable device | |
| 10: Body | 11: Channel |
| 12: Buffer solution | 20: Platinum wire |
| 30: Battery | |

The invention claimed is:

1. A method for isolating nucleic acid from whole blood without separate preprocessing, the method comprising:

providing a portable device having a body manufactured using a three-dimensional (3D) printer and made of a non-flammable material through which a current does not flow, a single linear channel defined on an upper surface of the body having a uniform polygonal cross-section, the channel having a groove with a predetermined size and configured to accommodate the whole blood and a buffer solution comprising a physiological saline solution, a first platinum wire and a second platinum wire, one end of the first platinum wire being in contact with one end of the channel, and one end of the second platinum wire being in contact with the other end of the channel, and a battery having a negative electrode and a positive electrode, the negative electrode being connected to the other end of the first platinum wire and the positive electrode being connected to the other end of the second platinum wire;

dropping the whole blood into the channel without separate preprocessing at a first location within 0.5 mm to 1.5 mm away from the one end of the first platinum wire connected to the negative electrode;

applying an electrical force to the negative and positive electrodes of the battery; and without a separate capture substrate, collecting the nucleic acid isolated from the whole blood that has moved toward the positive electrode at a faster rate than other blood components at a second location within the channel adjacent to the one end of the second platinum wire connected to the positive electrode.

2. The method of claim 1, wherein the channel has a buffer solution, which allows a non-preprocessed nucleic acid contained in the whole blood to move when a voltage is applied, and the nucleic acid isolated from the whole blood moves from the negative electrode to the positive electrode when the voltage is applied.

3. The method of claim 2, wherein the buffer solution is a physiological saline solution.

4. The method of claim 2, further comprises:

when a predetermined time passes after a predetermined voltage is applied to the channel, determining a substance adjacent to the positive electrode as the nucleic acid.

5. The method of claim 2, wherein the one end of the first platinum wire and the one end of second platinum wire, which are in contact with the channel, are immersed in the buffer solution with each having a length of 5 mm and a thickness of 0.3 mm.

6. The method of claim 2, further comprising:

manufacturing the body using a three-dimensional (3D) printer from a non-flammable material through which a current does not flow, wherein the body is an electrophoresis device.

7. The method of claim 1, wherein the body has a first predetermined width of 30 mm, a first predetermined length of 10 mm, and a first predetermined height of 4 mm, and the channel has a second predetermined width of 20 mm, a second predetermined length of 2 mm, and a second predetermined height of 2 mm.

8. The method of claim 1, wherein the isolated nucleic acid is collected at the second location within the channel that is 5 mm to 10 mm away from the one end of the second platinum wire.

* * * * *